United States Patent [19]
Lekholm et al.

[11] Patent Number: 5,421,345
[45] Date of Patent: Jun. 6, 1995

[54] METHOD AND APPARATUS FOR NON-INVASIVE IDENTIFICATION OF THE ENDOCORPOREAL SPATIAL DISTRIBUTION OF THE ELECTRICAL IMPEDANCE IN A SUBJECT

[75] Inventors: Anders Lekholm, Bromma, Sweden; Helmut Reichenberger, Eckental, Germany

[73] Assignee: Siemens Aktiengesellschaft, Munich, Germany

[21] Appl. No.: 164,715

[22] Filed: Dec. 10, 1993

[30] Foreign Application Priority Data

Dec. 22, 1992 [DE] Germany .................. 42 43 628.1

[51] Int. Cl.⁶ .................................................. A61B 5/00
[52] U.S. Cl. ..................................... 128/734; 128/693
[58] Field of Search ................ 128/644, 653.1, 660.06, 128/693, 723, 734, 774

[56] References Cited

U.S. PATENT DOCUMENTS

| | | | |
|---|---|---|---|
| 4,078,553 | 3/1978 | Duroux . | |
| 4,116,231 | 9/1978 | Matsuo | 128/734 |
| 4,578,635 | 3/1986 | Mee et al. | 128/734 X |
| 4,676,253 | 6/1987 | Newman et al. | 128/693 |
| 4,917,099 | 4/1990 | Stice | 128/734 X |
| 4,953,556 | 9/1990 | Evans | 128/693 X |
| 5,184,624 | 2/1993 | Brown et al. | 128/734 |
| 5,309,917 | 5/1994 | Wang et al. | 128/734 X |

FOREIGN PATENT DOCUMENTS

4104232  8/1992  Germany .

OTHER PUBLICATIONS

"Electrical Impedance Tomography and Biomagnetism," Webster, 8th International Conference on Biomagnetism, Book of Abstracts, pp. 287-288 (Aug. 18-24, 1991).

"Electrical Impedance Tomography; The Construction and Application to Physiological Measurement of Electrical Impedance Images," Brown et al., Medical Progress Through Technology, vol. 13, pp. 69-75 1987).

"Magnetic Imaging of Conductivity," Ahlfors et al., Proceeding of the Annual International Conference of the IEEE Engineering in Medicine and Biology Society, pp. 1717-1718 (Oct. 29-Nov. 1, 1992).

Primary Examiner—Sam Rimell
Attorney, Agent, or Firm—Hill, Steadman & Simpson

[57] ABSTRACT

In a method and apparatus for identifying the spatial distribution of electrical impedance within an examination subject, a source of electrical current is electrically connected to at least two feed electrodes which impress a feed current from the source in an examination region of a subject. The resulting magnetic field is measured at points outside the examination region, and an equivalent current density distribution is reconstructed within the examination region from the measured values of the magnetic field by an evaluation unit. A compensation conductor is connected to the current source. The current source delivers a compensation current, which flows in a direction opposite to the feed current, through the compensation conductor loop, so that the magnetic field generated by the feed current in the connecting lines is compensated. The evaluation unit identifies the spatial distribution of the impedance from the equivalent current density distribution. The spatial distribution of the impedance can be portrayed on a display.

21 Claims, 3 Drawing Sheets

METHOD AND APPARATUS FOR NON-INVASIVE IDENTIFICATION OF THE ENDOCORPOREAL SPATIAL DISTRIBUTION OF THE ELECTRICAL IMPEDANCE IN A SUBJECT

BACKGROUND OF THE INVENTION

1. Field of the Invention

The present invention is directed to an apparatus for identifying the spatial distribution of electrical impedance within an examination region of a living subject, as well as to a method for identifying the spatial distribution of electrical impedance within an examination region of a subject.

2. Description of the Prior Art

Various techniques and systems are known for identifying the spatial distribution of electrical impedance within an examination region of a living subject. Systems are known which have the following features.

A source of electrical current is connected via electrical connecting lines to at least two feed electrodes, the feed electrodes being suitable for impressing a feed current from a current source in an examination region of a subject. The impressed current causes a current distribution within the examination region, corresponding to the distribution of electrical impedance and to the position of the electrodes. A magnetic field measuring instrument is then used to acquiring a spatial distribution of characteristic quantities of the magnetic field which arises due to the aforementioned current distribution. This magnetic field is measured at measuring points outside the examination region. The output of the magnetic field measuring instrument is supplied to an evaluation unit, which reconstructs an equivalent distribution of the current density within the examination region based on the spatial distribution of the characteristic quantities. The equivalent current density distribution at the measuring points is that which would be generated by a theoretical magnetic field which best coincides with the measured magnetic field caused by the distribution of the current.

It is known to identify the electrical impedance within a subject non-invasively by means of so-called electrical impedance tomography as described, for example, in the article "Electrical Impedance Tomography and Biomagnetism," Webster, published in Book of Abstracts, 8th International Conference on Biomagnetism, Muenster, Aug. 18–24, 1991, or in the article "Electrical Impedance Tomography; the Construction and Application to Physiological Measurement of Electrical Impedance Images," Brown et al., published in Medical Progress Through Technology 13, pp. 69–75, 1987 Yartinus Nijhoff Publishers, Boston.

In this known techniques, alternating currents having frequencies in the range from 10 through 50 kHz are impressed on the body via electrodes applied to the subject. Tomograms of the conductivity distribution or impedance distribution are calculated in a tomographic reconstruction from the differences in potential which thereby arise between the electrodes.

Published electrical impedance values available in the literature, which were acquired ex vivo or in the course of one-time in vivo examinations, preferably on an animal model, are usually used for producing body-adapted models. The relative magnitude in specific body regions as well as the chronological variation of electrical impedance can be directly consulted for making a medical diagnosis. For example, in vessel or tumor diagnostics as well as in combination with the administration of medications or other therapy measures, deviations of the electrical impedance from standard values, or standard distributions, can be evaluated.

It is proposed in the article "Magnetic Imaging of Conductivity," Ahlfors et al., Proceedings of the Annual International Conference of the IEEE Engineering in Medicine and Biology Society, Vol. 14, Paris, France, Oct. 29–Nov. 1, 1992 Part 5, pp. 1717–1718, that a current be impressed on a subject via surface electrodes for identifying the conductivity distribution of the subject, and that the magnetic field generated thereby then be evaluated. It is assumed in this article that only small deviations from a prescribed conductivity distribution occur in the examination region. It is assumed in a further approximation that the magnetic field varies in the same way, as though an additional, equivalent current density distribution were present in the examination region. This additional, equivalent current density distribution is identified by means of a minimum norm estimate from the inverse solution of the measured magnetic field distribution with localization methods which are employed in the field of biomagnetism. The conductivity changes are identified from the equivalent current density distribution, by dividing the equivalent current density distribution by the electrical field of prescribed conductivity distribution, without taking the deviations into consideration.

It has now been shown that the measured values, heretofore thought to arise primarily due to the characteristics of the subject, are in fact dominated by the magnetic field of the entire conductor loop which includes the connecting feed lines, so that a non-uniform current density in the examination region can only be acquired as weak measured values. The magnetic field arising from the connecting lines could be compensated, for example, by subtracting a calculated or measured value corresponding to the contribution of the connecting lines. This would result, however, in a very low sensitivity of the apparatus.

SUMMARY OF THE INVENTION

It is an object of the present invention to provide an apparatus for identifying the spatial distribution of electrical impedance in a subject which has a high sensitivity for the magnetic fields generated by the distribution of current in the examination region.

It is a further object to specify a method for identification of the spatial distribution of the electrical impedance in a subject with a high degree of sensitivity.

The above objects are achieved in a method and apparatus wherein a compensation conductor loop is connected to the source of electrical current, the electrical current source delivering a compensation current which flows in a direction opposite to the feed current through the compensation conductor loop. The magnetic field generated by the feed current in the connecting lines is thereby compensated. The evaluation unit includes means for identifying the spatial distribution of the impedance from the equivalent current density distribution, and is connected to a display which presents a visual portrayal of the spatial distribution of the impedance.

In a further embodiment of the method and apparatus, at least some of the feed electrodes are annular. In this embodiment it is thus possible to supply the current to the examination region over a large area, which results in the direction of the current density within the examination region not being subject to excessively large fluctuations.

In a further embodiment of the invention, at least some of the feed electrodes are also electrically connected to the means for measuring potential. Because the feed electrodes simultaneously represent equipotential areas at the surface, it is assured that they do not falsify the distribution of potential at the surface.

A greater flexibility for the measurement of potential is achieved in an embodiment wherein the means for measuring potential includes potential-measuring electrodes which are connected only to the means for measuring potential. Given large-area potential-measuring electrodes, care must be exercised to ensure that the electrodes are applied, as far as possible, to equipotential areas in order to avoid falsifications of the measured values.

In a further embodiment, a control unit is connected to the current source, so that the current supplied by the current source is triggerable by means of the control unit coordinated with a periodic activity of the subject. Fluctuations of the impedance distribution within the examination region due to respiration or cardiac activity can thus be blanked out, or can be designationally evaluated. For example, reconstructions of the distribution of impedance in the "inhaled" and "exhaled" states of the upper body can be placed in relationship to one another. In order to improve the signal-to-noise ratio, an averaging of values measured at identical points in time within the successive cycles of the periodic activity can be undertaken.

In a further embodiment of the invention, the current supplied by the current source is an alternating current having a frequency up to approximately 1 Hz through 1 kHz. Due to the frequency-dependency of the electrical impedance of tissue, the measurement is preferably undertaken in the region wherein the bioelectrical and biomagnetic fields arise.

The apparatus and method can be employed for identifying the impedance distribution in the upper body or in a body extremity, because a substantially uniform field flux is present, given an adequate distance from the examination region.

DESCRIPTION OF THE PREFERRED EMBODIMENTS

Figure 1:
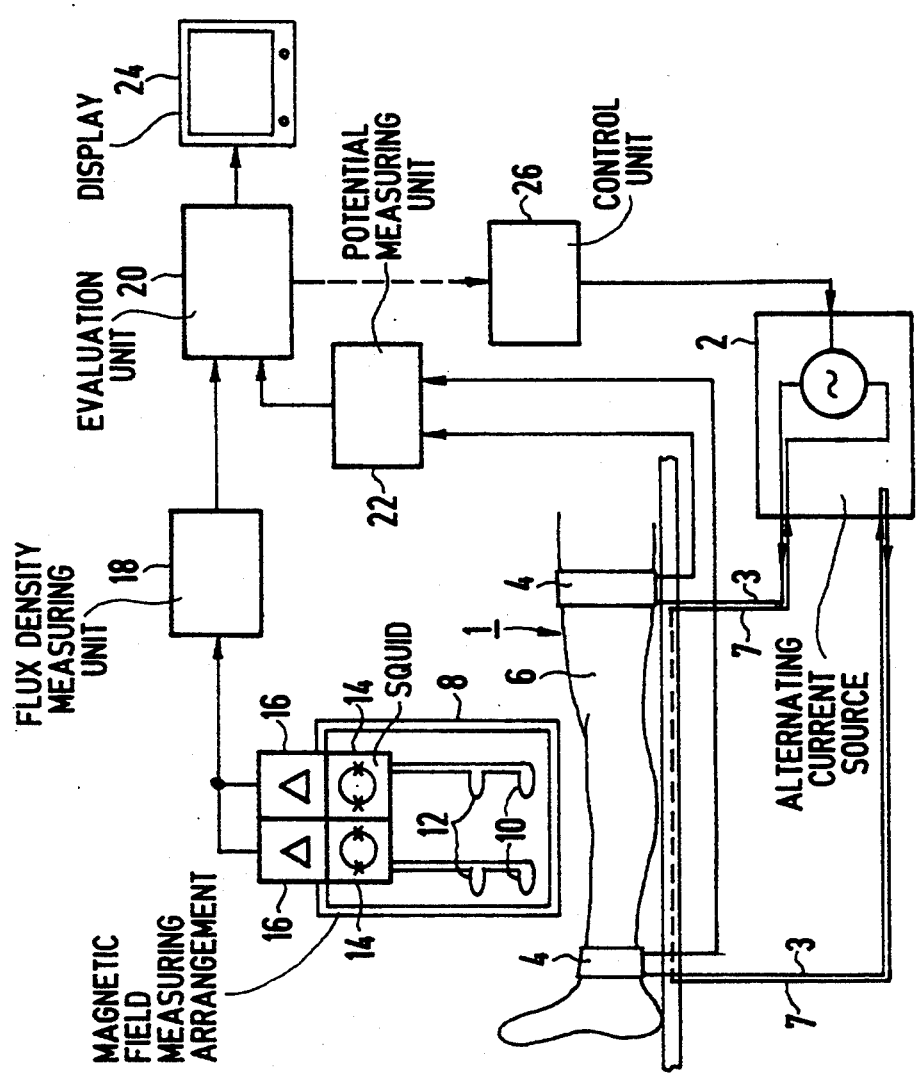
FIG. 1 is a schematic illustration of a first embodiment of an apparatus for the non-invasive identification of the electrical impedance of an extremity of an examination subject, constructed and operating in accordance with the principles of the present invention.

An apparatus for identifying the spatial distribution of electrical impedance within an examination region 1 of a subject is shown in FIG. 1, in the form of a block diagram. The apparatus includes an electrical alternating current source 2, which is conductively connected to two feed electrodes 4 via electrical connecting lines 3. The feed electrodes 4 are in the form of annular electrodes, and are suitable for impressing an alternating current supplied from the current source 2 into at least a part of an extremity 6, which in this embodiment forms the examination region 1. In this embodiment, the extremity 6 is the lower part of a leg of the subject. It is also possible, however, to adapt the feed electrodes 4 to an upper leg or parts of an arm. When a current is impressed into the examination region 1 by the alternating current source 2 via the feed electrodes 4, a current density distribution arises within the examination region 1 which in turn causes a magnetic field to arise. The resulting current density distribution and magnetic field are dependent on the distribution of the electrical impedance within the examination region 1 and the position of the feed electrodes 4 with respect to the examination region 1.

The electrical connecting lines 3 generate their own magnetic field. For compensating the magnetic field generated by the electrical connecting lines 3, a compensation conductor loop 7, connected in series with the connecting lines 3 in the current source 2, is arranged parallel to the connecting lines 3. It is thus assured that a compensation current flowing in the compensation conductor loop 7 corresponds to the feed current in terms of amplitude and phase. The compensation loop 7 is arranged in the patient support in the region of the examination region 1, as indicated by dashed lines. The compensation conductor loop 7 can alternatively be provided as a separate, planar element disposed in the area of the examination region 1.

The spatial distribution of characteristic quantities of the magnetic field principally generated by the current distribution in the examination region I such as, for example, the flux density or the flux density gradient, is acquired with a magnetic field measuring arrangement 8 at a number of measuring points outside the examination region 1. In the embodiment of FIG. 1, a multi-channel gradiometer arrangement is provided as the magnetic field measuring arrangement 8. The flux density gradient is measured simultaneously by this arrangement at thirty-seven spatial points or measuring points with this arrangement. In order to increase the number of measuring points, the measuring position of the multi-channel gradiometer arrangement can be varied. It should be noted that the spatial distribution can be successively identified at a number of points, using a single-channel measuring arrangement.

Each channel of the multi-channel gradiometer arrangement includes a field coil 10 and a compensation coil 12 arranged axially spaced from the field coil 10. The compensation coil 12 is coupled to a SQUID 14 (Superconducting Quantum Interference Device). Each channel also includes a pre-amplifier 16, through which the signal generated by the SQUID 14 is supplied to a flux density measuring unit 18. For clarity, only two of the thirty-seven channels of the multi-channel gradiometer arrangement are shown in FIG. 1. The flux density measuring unit 18 processes the gradiometer signals to form flux density signals. An equivalent current density distribution in the examination region 1 is reconstructed from the spatial distribution of the flux density in an evaluation unit 20. This equivalent density distribution is derived so as to generate a theoretical magnetic field which coincides as closely as possible to magnetic field measured at the measuring points. A reconstruction method disclosed, for example, by Hämäläinen et al. in Report TKK-F-A559 (1984) entitled "Interpreting Measured Magnetic Fields of the Brain" (ISBN 951-753-362-4) can be used for reconstructing the current density distribution. This method can also be utilized in the localization of electrophysiological activities.

At the same time as the measurement of the spatial distribution of the magnetic field is made, the potential at the surface of the examination region 1 is acquired with a potential measuring unit 22. The measured potential values supplied by the potential measuring unit 22 are also supplied to the evaluation unit 20. Whereas the distribution of the current density is only a measure for the relative distribution of the electrical impedance, an absolute identification of the impedance is possible by taking differences in potential into consideration, and undertaking a normalization with respect to the overall impressed current.

The spatial distribution of the impedance identified in the evaluation unit 20 is supplied in the form of electrical signals to a display 24, or to a recorder for registration thereof.

Because, among other things, cardiac activity is reflected in the spatial distribution of electrical impedance, i.e., the distribution varies dependent on cardiac activity, a measurement which is synchronized with the cardiac cycle offers further diagnostic possibilities. To that end, the evaluation unit 20 forms a signal from the measured values which is characteristic of cardiac activity. The characteristic cardiac signal is supplied to a control unit 26, which triggers the current source 2. This permits disturbing influences to be reduced by undertaking an averaging synchronized with the cardiac cycle, and also permits further diagnostic information to be obtained such as, for example, differential measurements or differential formation of current density distributions, from various regions within the cardiac cycle. The signal characteristic of the cardiac activity can be obtained using an EKG apparatus (not shown) in a known manner.

Figure 2:
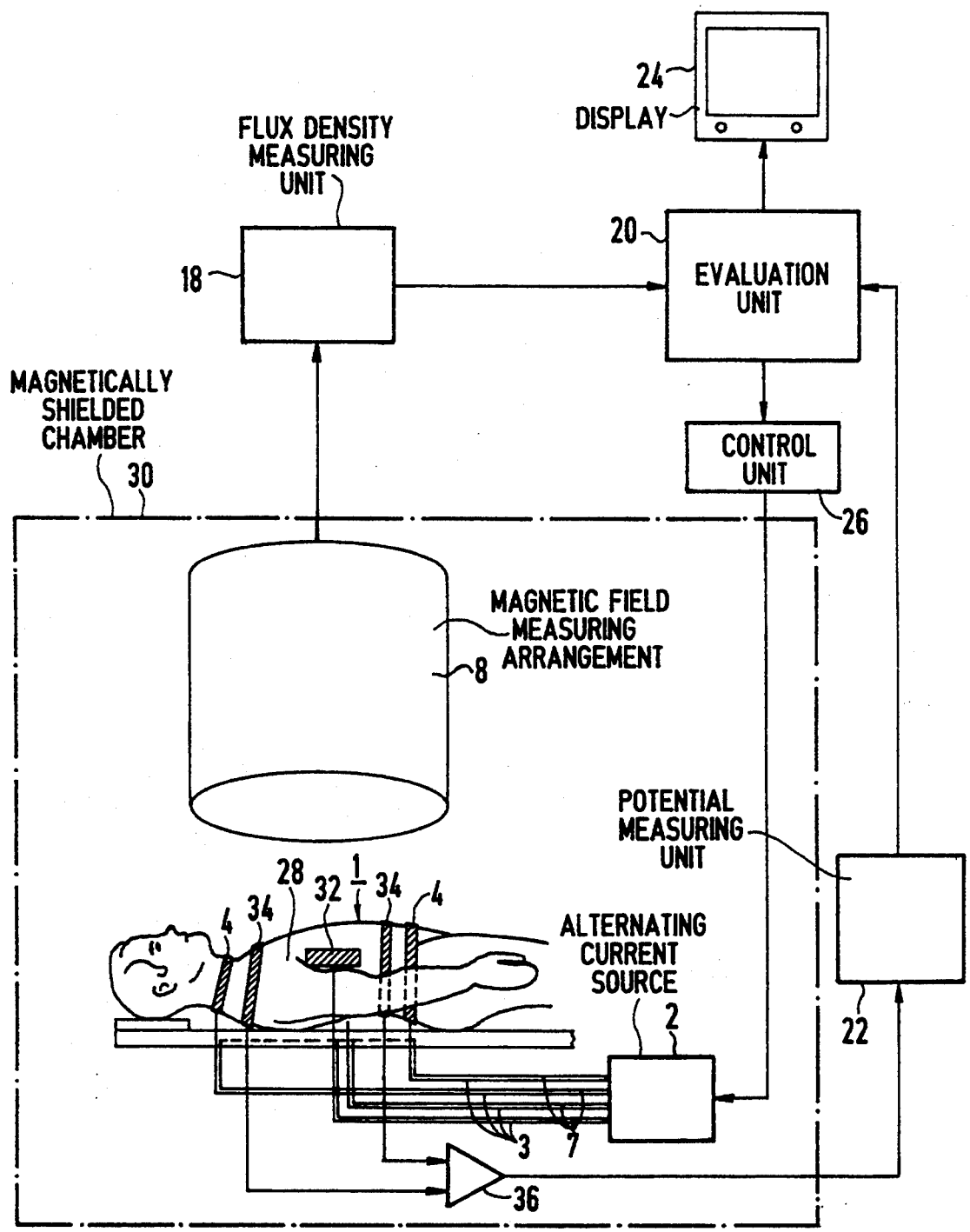
FIG. 2 is a schematic illustration of a second embodiment of an apparatus for the non-invasive identification of the electrical impedance of the upper body of an examination subject, constructed and operating in accordance with the principles of the present invention.

The embodiment shown in FIG. 2 is an apparatus for non-invasive identification of electrical impedance within the upper body 28 of a subject. In this embodiment, the arrangement 8 for measuring magnetic fields, further electrical components, and a patient or subject are situated in a magnetically shielded chamber 30. This permits the measurement of extremely small magnetic fields, so that the impressed currents can be maintained low. Differing from the apparatus of FIG. 1, the embodiment of FIG. 2 employs two lateral electrodes 32 in addition to the annular feed electrodes 4. The lateral electrodes 32 are arranged respectively at the right and left sides of the patient, in the region of the armpits, the lateral electrodes 32, as the annular feed electrodes 4, are connectable to the current source 2. Again, compensation conductor loops 7 are arranged parallel to the connecting lines 3.

The measurement of the electrical potentials ensues via two electrodes 34 for measuring potentials, which are separated from the feed electrodes 4 and which can obtain a value for the potential at the surface of the examination region 1, approximately parallel to the annular feed electrodes 4.

In order to avoid unwanted influences on the cardiac activity of the patient, the current source 2 supplies only extremely low currents into the examination region 1, so that the differences in potential are correspondingly very small. An amplifier 36, through which the potential signal is supplied to the potential measuring unit 22, is therefore provided for amplifying the difference in potential.

The use of the feed electrodes 32 permits the identification of the impedance distribution transversely relative to the upper body or thorax in a further, independent measurement.

Again, a characteristic signal, which may be more highly modulated, can be calculated from the measured magnetic field signals for evaluating cardiac and/or respiratory activity.

Figure 3:
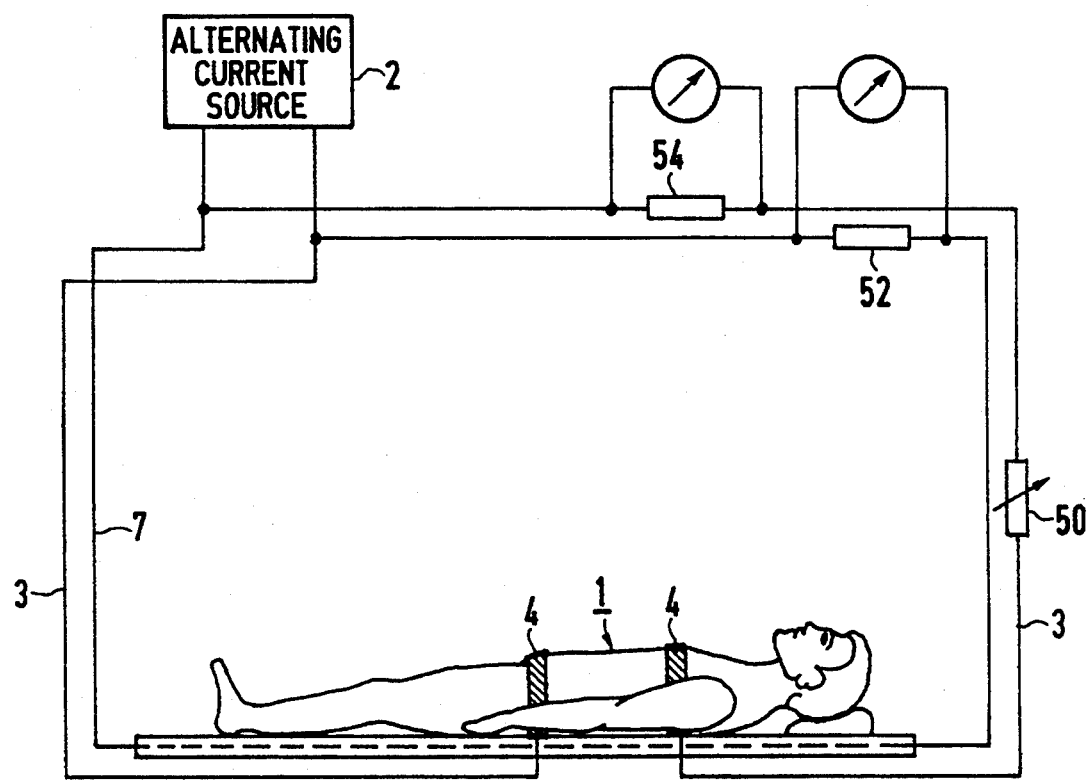
FIG. 3 shows an electrical parallel circuit of connecting lines and compensation conductor loops having current balancing means.

A further version of the compensation conductor loop 7 is shown in FIG. 3. The version of FIG. 3 differs from that shown in FIG. 1 in that the conductor loop 7 is not connected in series with the connecting lines 3, but is instead parallel to the connecting lines 3. In order to maintain the compensation current identical to the feed current in terms of amplitude and phase, a balancing element 50 is provided, which contains a variable, ohmic, capacitive and inductive resistor. Two resistors 52 and 54, across which the voltage is acquired, are provided for measuring the current. Balancing can then take place, for example, using an oscilloscope, to which the voltages across the resistors 52 and 54 are supplied.

Figure 4:
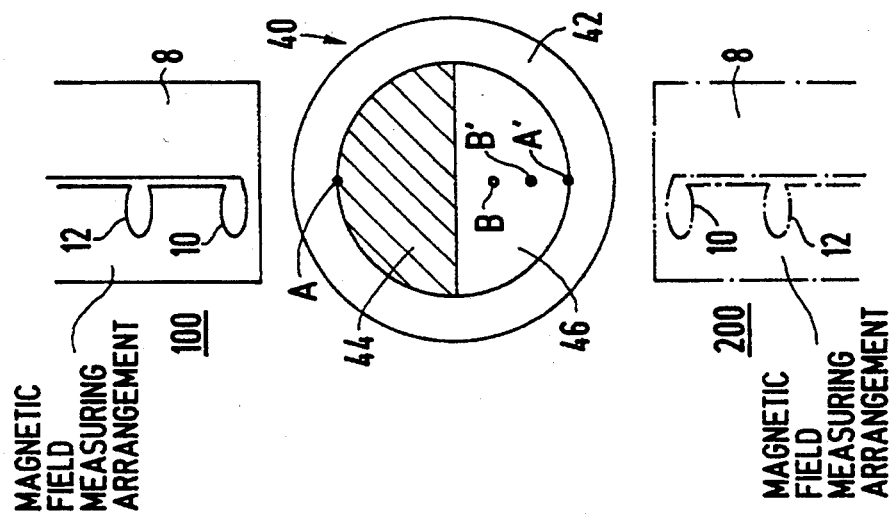
FIG. 4 shows a simplified model of an extremity for estimating the resulting currents and magnetic flux densities therein.

The region in which the electrical and magnetic quantities lie can be estimated with reference to a highly simplified model of an extremity shown in FIG. 4. FIG. 4 shows a circular cross section 40 taken through an extremity. The cross section 40 is surrounded by skin and fatty tissue 42, and has an interior which is symmetrically divided into bone 44 and muscle 46. The cross section 40 has a diameter of 12 cm. The thickness of the ring 42 of skin and fatty tissue is approximately one-sixth of the total diameter, i.e., 2 cm. The arrangement 8 for measuring magnetic fields is preferably situated in a first measuring position indicated at 100 above the model, with the field coil 10 of the gradiometer being disposed at a distance of 2 cm from the model. It is further assumed that an overall current of 10 $\mu$A flows through the cross section 40, with the current through the bone part 44 being left out of consideration. The specific conductivities or equivalent conductivity are 5 mS/cm for muscle and 0.4 mS/cm for fat.

Due to the current distribution, a current IM=8.3 $\mu$A flows in the muscle, and a current IF=1.7 $\mu$A flows in the skin and fat ring 42.

In position 100, the field coil 10 sees the current IF concentrated roughly at point A and sees the current IM concentrated roughly at point B. The overall flux density which the field coils pick up in the first measuring position 100 is thus equal to B1=8.5pT+16.5pT=25pT In a second measuring position 200 (shown with dashed lines) of the magnetic field measuring arrangement 8, the field coil 10 sees the current IF roughly concentrated at the position A', and sees the current IM roughly in the position B', A flux density of B2=8.5pT+29pT=38pT thus arises for the measuring position 200.

These measured values are obtained by measurements made with a respective measuring channel at the two measuring positions 100 and 200. Again, a reconstruction of the current density distribution could be calculated by an inverse solution technique, after increasing the number of measuring positions and/or by employing a multi-channel measuring arrangement.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for identifying the endocorporeal spatial distribution of the electrical impedance in an examination region of a subject, comprising:

an electric current source which generates a feed current;

two feed electrodes respectively connected to said current source by electrical connecting lines which carry said feed current, said connecting lines having a first magnetic field associated therewith due to said feed current carried therein, said feed electrodes being attachable to a subject and forming means for impressing said feed current into an examination region of said subject and causing a distribution of current in said examination region dependent on the electrical impedance distribution in said examination region and the position of said feed electrodes, said distribution of current causing a second magnetic field;

a compensation conductor Iccp connected to said current source;

said current source including means for supplying a compensation current to said compensation conductor Iccp having a direction opposite to said feed current for compensating said first magnetic field;

magnetic field measuring means for obtaining a spatial distribution of a characteristic quantity of said second magnetic field at a plurality of points outside said examination region;

evaluation means, supplied with said spatial distribution of a characteristic quantity, for reconstructing, from said spatial distribution of a characteristic quantity, an equivalent current density distribution in said examination region which would generate a theoretical magnetic field most closely coinciding with said second magnetic field, said evaluation means including means for identifying the spatial distribution of impedance in said examination region from said equivalent current density distribution; and display means connected to said evaluation means for visually portraying said spatial distribution of impedance.

2. An apparatus as claimed in claim 1 wherein said compensation conductor loop is disposed substantially parallel to said connecting lines and to said distribution of current in said examination region.

3. An apparatus as claimed in claim 1 wherein said connecting lines and said compensation conductor loop are electrically connected in series.

4. An apparatus as claimed in claim 1 wherein said connecting lines and said compensation conductor loop are electrically connected in parallel, and further comprising balancing means electrically connected in said compensation conductor loop for equalizing said feed current and said compensation current in amplitude and phase.

5. An apparatus as claimed in claim 1 further comprising:

potential measuring means, connected to said evaluation means, for measuring a distribution of electrical potential existing at a surface of said examination region caused by said distribution of current impressed in said examination region; and wherein said means for identifying the spatial distribution of impedance from said distribution of current density in said examination region comprises means for identifying the spatial distribution of impedance from aid distribution of current density in said examination region and from said distribution of electrical potential at said surface of said examination region.

6. An apparatus as claimed in claim 5 wherein at least one of said feed electrodes is electrically connected to said potential measuring means.

7. An apparatus as claimed in claim 5 wherein said potential measuring means includes potential-measuring electrodes exclusively used by said potential measuring means.

8. An apparatus as claimed in claim 1 wherein at least one of said feed electrodes is annular.

9. An apparatus as claimed in claim 1 further comprising:

control means connected to said current source for triggering said feed current and said compensation current dependent on a periodic activity of said subject.

10. An apparatus as claimed in claim 1 wherein said current source comprises an alternating current source having a frequency in the range of 1 Hz through 1 kHz.

11. An apparatus as claimed in claim 1 wherein said magnetic field measuring means comprises a multi-channel magnetic field measuring means.

12. An apparatus as claimed in claim 1 wherein said feed electrodes have a shape conforming to an upper body region of said subject, and wherein said examination region comprises said upper body region.

13. An apparatus as claimed in claim 1 wherein said feed electrodes have a shape conforming to an extremity of said examination subject, and wherein said examination region comprises said extremity.

14. A method for identifying the endocorporeal spatial distribution of the electrical impedance in an examination region of a subject, comprising the steps of:

generating a feed current carried by electrical connecting lines, said connecting lines having a first magnetic field associated therewith due to said feed current carried therein;

attaching feed electrodes, connected to said connecting lines, to a subject and impressing said feed current into an examination region of said subject and causing a distribution of current in said examination region dependent on the electrical impedance distribution in said examination region and the position of said feed electrodes, said distribution of current causing a second magnetic field;

supplying a compensation current to a compensation conductor loop in a direction opposite to said feed current for compensating said first magnetic field;

obtaining a spatial distribution of a characteristic quantity of said second magnetic field at a plurality of points outside said examination region;

reconstructing, from said spatial distribution of a characteristic quantity, an equivalent current density distribution in said examination region which would generate a theoretical magnetic field most closely coinciding with said second magnetic field;

identifying the spatial distribution of impedance in said examination region from said equivalent current density distribution; and visually portraying said spatial distribution of impedance.

15. A method as claimed in claim 14 comprising the additional step of disposing said compensation conductor loop substantially parallel to said connecting lines and to said distribution of current in said examination region.

16. A method as claimed in claim 14 comprising the additional step of connecting said connecting lines and said compensation conductor loop in series.

17. A method as claimed in claim 14 comprising the additional step of connecting said connecting lines and said compensation conductor loop in parallel.

18. A method as claimed in claim 14 comprising the additional steps of:

measuring a distribution of electrical potential existing at a surface of said examination region caused by said distribution of current impressed in said examination region; and identifying the spatial distribution of impedance from a distribution of current density in said examination region and from said distribution of electrical potential at said surface of said examination region.

19. A method as claimed in claim 14 comprising the additional step of:

triggering said feed current and said compensation current dependent on a periodic activity of said subject.

20. A method as claimed in claim 14 wherein the step of attaching said feed electrodes to said subject is further defined by attaching said feed electrodes to an upper body region of said subject, and wherein said examination region comprises said upper body region.

21. A method as claimed in claim 14 wherein the step of attaching said feed electrodes to said subject is further defined by attaching said feed electrodes to an extremity of said examination subject, and wherein said examination region comprises said extremity.

* * * * *